(12) United States Patent
Hongtao et al.

(10) Patent No.: US 11,649,572 B2
(45) Date of Patent: May 16, 2023

(54) MEDICATED THREAD MANUFACTURING SYSTEM AND MEDICATED THREAD MANUFACTURING METHOD

(71) Applicant: LongHua Hospital Shanghai University of Traditional Chinese Medicine, Shanghai (CN)

(72) Inventors: Liang Hongtao, Shanghai (CN); Wang Chen, Shanghai (CN); Yao Yibo, Shanghai (CN); Tao Xiaochun, Shanghai (CN); Cao Yongqing, Shanghai (CN); Lu Jingen, Shanghai (CN)

(73) Assignee: LongHua Hospital Shanghai University of Traditional Chinese Medicine, Shanghai (CN)

( * ) Notice: Subject to any disclaimer, the term of this patent is extended or adjusted under 35 U.S.C. 154(b) by 0 days.

(21) Appl. No.: 17/528,899

(22) Filed: Nov. 17, 2021

(65) Prior Publication Data

US 2022/0333277 A1    Oct. 20, 2022

(30) Foreign Application Priority Data

Apr. 15, 2021   (CN) .......................... 202110405107.4

(51) Int. Cl.
    *D02G 3/28*        (2006.01)
    *D02G 3/36*        (2006.01)
    (Continued)

(52) U.S. Cl.
    CPC ................ *D02G 3/28* (2013.01); *D02G 3/36* (2013.01); *D02G 3/448* (2013.01); *D02G 1/02* (2013.01); *D10B 2509/00* (2013.01)

(58) Field of Classification Search
CPC .. D02G 3/08; D02G 3/28; D02G 3/36; D02G 3/448
See application file for complete search history.

(56) References Cited

U.S. PATENT DOCUMENTS

| 730,516 | A | * | 6/1903 | Culver | ................... | B65H 54/56 |
| | | | | | | 57/26 |
| 1,275,103 | A | * | 8/1918 | Swanson | ................... | D03D 3/00 |
| | | | | | | 28/143 |

(Continued)

*Primary Examiner* — Shaun R Hurley
(74) *Attorney, Agent, or Firm* — Taft Stettinius & Hollister LLP (57) ABSTRACT

A medicated thread manufacturing system and associated method includes first and second slideways, a thread clamping apparatus and a medicine spraying apparatus slidably arranged on the first slideway, and a thread winding apparatus slidably arranged on the second slideway. The clamping apparatus clamps two ends of a to-be-processed medicated thread, straightens the thread and twists the thread in the straightened state into a single-strand rope state. The spraying apparatus sprays a medicine towards a surface layer of the thread in the straightened state. The winding apparatus abuts a center position of the thread in the single-strand rope state, pulls and folds the thread, and rotates the thread such that the thread winds and extends from middle to two ends to be twisted in a double-strand rope state. A control apparatus is in signal connection and/or electrical connection to the clamping apparatus, the spraying apparatus and the winding apparatus.

10 Claims, 6 Drawing Sheets

(51) Int. Cl.
*D02G 3/44* (2006.01)
*D02G 1/02* (2006.01)

(56) References Cited

U.S. PATENT DOCUMENTS

| | | | | | |
|---|---|---|---|---|---|
| 3,315,458 | A | * | 4/1967 | Alexander | D07B 7/162 57/22 |
| 4,161,861 | A | * | 7/1979 | Storm | D07B 7/162 57/22 |
| 4,207,928 | A | * | 6/1980 | Pershin | D07B 3/005 140/149 |
| 5,517,813 | A | * | 5/1996 | Klundt | B21F 15/04 57/26 |
| 5,852,924 | A | * | 12/1998 | Mulligan | A01K 91/16 57/26 |
| 5,960,581 | A | * | 10/1999 | Schneider | A01K 91/16 57/25 |
| 2016/0355981 | A1 | * | 12/2016 | Chtourou | B31F 1/0074 |
| 2017/0350071 | A1 | * | 12/2017 | Mabuchi | B21F 15/04 |
| 2018/0057971 | A1 | * | 3/2018 | Roh | D02G 3/28 |
| 2019/0214165 | A1 | * | 7/2019 | Mabuchi | H01B 13/02 |

* cited by examiner

MEDICATED THREAD MANUFACTURING SYSTEM AND MEDICATED THREAD MANUFACTURING METHOD

CROSS REFERENCE TO RELATED APPLICATIONS

This application claims priority to Chinese Patent Application No. CN 202110405107.4 filed Apr. 15, 2021, the contents of which are hereby incorporated by reference in their entirety.

FIELD OF TECHNOLOGY

The present invention relates to the technical field of medicated thread apparatuses, in particular to a medicated thread manufacturing system and medicated thread manufacturing method.

BACKGROUND

A medicated thread is commonly known as a spill of rolled paper or a medicinal fuse, and most conventional medicated threads are manufactured by mulberry paper. A medicated thread therapy is one of drainage methods in surgery of traditional Chinese medicine. A medicine is externally adhered to a surface layer of the medicated thread or is wrapped in the medicated thread, then the medicated thread is inserted into a perforated ulcer, and necrotic tissues are attached to the medicated thread by means of linear shapes of the medicine and the medicated thread, thereby guiding pus to drain externally. Drained by the medicated thread, it has the advantages of being convenient to operate, being convenient for a patient to replace the medicated thread by himself or herself, light in pain and the like. The medicated thread is in particular suitable for people with ulcer in the middle and later periods where wounds are too deep and too smaller and it is hard to drain pus or people with bag pus, a cavity, chronic fistula and a sinus tract.

A conventional medicated thread is generally prepared by tailoring the mulberry paper manually according to a certain specification and manually twisting the mulberry paper. However, the twisting process is time-wasting and labor-wasting. As the medicated thread is wide in application range and excellent in treatment effect, the demand on the medicated thread is increased with each passing day, and a trend of demand exceeding supply of the medicated thread occurs as the medicated thread is twisted manually. Furthermore, hands of a staff twisting the medicated thread for a long time are damaged to a different extent due to friction and other external factors, and even, interphalangeal arthritis and the like are initiated. In particular, the twisting process of some thicker and longer medicated threads is higher in difficulty, thereby bringing great health hazard to the staff. Furthermore, as the medicated thread is twisted manually, some bacteria are brought to the medicated thread because the hands are not cleaned thoroughly. For example, as sweat stains of the hands are immerged into the medicated thread, color and shape of the medicated thread are changed and some external dirt is brought, such that the wound of the patient is polluted secondarily as sanitation of the medicated thread is not guaranteed. As a result of technical difference of the staff, even through different staffs manufacture the medicated threads of same model, a problem of different dimensions may exist, and whether the quality of a product is qualified or not cannot be ensured.

Based on improvement of the conventional medicated thread manufacturing process, in the prior art, a machine special for twisting the medicated thread emerges. However, according to the machine, a rotating wheel is rotated manually, such that the mulberry paper is twisted into the rope state, and the machine is further manually operated to fold the medicated thread and twist the medicated thread into the double-strand rope state. It can be known that the machine only plays a role of fixing the medicated thread, such that the manufactured medicated thread meets the qualified demand in dimension, precision and cleanliness. But the specific operating processes are accomplished manually, so that the machine is low in efficiency and time-wasting and labor-wasting. Medicine spraying is another independent step after the medicated thread is manufactured, so that time and cost are wasted.

Thus, in recent years, the applicant devotes himself/herself to developing an automatic medicated thread manufacturing system which does not need artificial participation in the medicated thread manufacturing process, improves the medicated thread manufacturing efficiency and the quality of the product and adds an automatic medicine spraying step in the medicated thread manufacturing process.

SUMMARY

It is thereof an object of the present invention to provide a medicated thread manufacturing system and medicated thread manufacturing method. In the medicated thread manufacturing process, artificial participation is not needed, such that the medicated thread manufacturing efficiency and the quality of the product are improved greatly. In the medicated thread manufacturing process, the automatic medicine spraying step is added, and multiple steps are integrated, such that automation of medicated thread manufacturing is realized.

A technical scheme provided by the present invention is as follows:

A medicated thread manufacturing system, including:

a first slideway and a second slideway that are arranged in a T shape;

a thread clamping apparatus and a medicine spraying apparatus slidably arranged on the first slideway;

wherein the thread clamping apparatus is used for clamping two ends of a to-be-processed medicated thread, straightening the to-be-processed medicated thread and twisting the to-be-processed medicated thread in the straightened state into a single-strand rope state, and the medicine spraying apparatus is used for spraying a medicine toward a surface layer of the to-be-processed medicated thread in the straightened state;

a thread winding apparatus slidably arranged on the second slideway, wherein the thread winding apparatus is used for abutting a center position of the to-be-processed medicated thread in the single-strand rope state and pulling the to-be-processed medicated thread towards a direction opposite to the first slideway to fold the to-be-processed medicated thread, and used for rotating, such that the to-be-processed medicated thread winds and extends from middle to two ends to be twisted in a double-strand rope state; and a control apparatus in signal connection and/or electrical connection to the thread clamping apparatus, the medicine spraying apparatus and the thread winding apparatus to control the matching opportunity of the thread clamping apparatus, the medicine spraying apparatus and the thread winding apparatus.

In the technical scheme, the first slideway and the second slideway are arranged in T shape, such that it is convenient to match the thread clamping apparatus, the medicine spraying apparatus and the thread winding apparatus. The thread clamping apparatus is controlled by the control apparatus to straighten the to-be-processed medicated thread, such that the to-be-processed medicated thread is in a tightened state, and it is convenient to spray the medicine to the surface layer thereof by the medicine spraying apparatus, such that the medicine can be attached to all areas in the surface layer of the to-be-processed medicated thread. If the to-be-processed medicated thread is in a bended state, a wrinkle area appears. When the medicine is sprayed, the wrinkle area cannot be covered with the medicine, such that the using effect is not good enough. The thread winding apparatus is controlled by the control apparatus again to twist the to-be-processed medicated thread sprayed with the medicine into the single-strand rope state, and the thread winding apparatus is further controlled to pull the to-be-processed medicated thread, such that the to-be-processed medicated thread is folded to further drive the to-be-processed medicated thread to rotate, and therefore, the to-be-processed medicated thread winds and extends from middle to two ends to be twisted into the double-strand rope state. During a process, the to-be-processed medicated thread is in the tightened state all the time, such that a condition that the to-be-processed medicated thread is floppy in the twisting process is avoided effectively, and therefore, every part thereof is stressed uniformly, thereby meeting a clinical demand. The control apparatus further can control strokes of the thread clamping apparatus, the medicine spraying apparatus and the thread winding apparatus, such that it can be further used for manufacturing medicated threads with different lengths and thicknesses, thereby meeting the clinical demands of different patients. Further, in the whole course of manufacturing the medicated thread by the medicated thread manufacturing system, artificial participation is not needed, such that the cleanliness of the medicated thread product is improved greatly.

Further, preferably, the first slideway is provided with a first slide rail and a second slide rail that are arranged parallelly;

the thread clamping apparatus is slidably arranged on the first slide rail; and the medicine spraying apparatus is slidably arranged on the second slide rail.

Further, preferably, the thread clamping apparatus includes a first clamping mechanism, a second clamping mechanism and a first driving mechanism;

both the first clamping mechanism and the second clamping mechanism are in signal connection and/or electrical connection to the control apparatus, both the first clamping mechanism and the second clamping mechanism are slidably connected with the first slide rail and are used for clamping two ends of the to-be-processed medicated thread respectively, and the first driving mechanism is assembled at one end of the first slide rail and is used for driving the first clamping mechanism and the second clamping mechanism to move close to each other or far away from each other; and wherein when the to-be-processed medicated thread is in the straightened state, the first clamping mechanism is further used for twisting the to-be-processed medicated thread into the single-strand rope state.

Further, preferably, the first clamping mechanism includes a first sliding seat, a first clamping seat and a first driving part;

the second clamping mechanism includes a second sliding seat and a second clamping seat;

both the first sliding seat and the second sliding seat are slidably connected to the first slide rail, the first driving part is in signal connection and/or electrical connection to the control apparatus and is assembled on the first slide rail and the first clamping seat is assembled at a driving end of the first driving part, and the second clamping seat is assembled on the second sliding seat and is arranged opposite to the first clamping seat;

wherein the first clamping seat and the second clamping seat are used for clamping two ends of the to-be-processed medicated thread respectively, and when the to-be-processed medicated thread is in the straightened state, the first driving part drives the first clamping seat to rotate to twist the to-be-processed medicated thread into the single-strand rope state.

Further, preferably, the first clamping mechanism includes a first clamping body and a first clamping head;

The first clamping body is assembled at the driving end of the first driving part, the first clamping head is elastically assembled at an end, opposite to the first driving part, of the first clamping body, the first clamping head is used for clamping one end of the to-be-processed medicated thread, and moves toward the second clamping seat under the action of a tensile force of the to-be-processed medicated thread and is restored to an initial position under the action of an elastic force after the tensile force is canceled; and the second clamping mechanism includes a second clamping body and second clamping head;

the second clamping body is assembled on the second sliding seat, the second clamping head is elastically assembled at an end, facing the second clamping body, of the second clamping body, the second clamping head is used for clamping the other end of the to-be-processed medicated thread, and moves toward the first clamping seat under the action of a tensile force of the to-be-processed medicated thread and is restored to the initial position under the action of the elastic force after the tensile force is canceled; and wherein in a process that the to-be-processed medicated thread in the straightened state is twisted into the single-strand rope state, a length thereof is shortened gradually, and the first clamping head and the second clamping head provide an elastic force for keeping the to-be-processed medicated thread tight.

Further, preferably, the first driving mechanism includes a first driving body, two first belt wheels and a first conveyor belt;

the first driving body is assembled at one end of the first slideway and is in signal connection and/or electrical connection to the control apparatus, one of first belt wheels is assembled at the driving end of the first driving body and corresponds to a position of the first slide rail, the other one of first belt wheels is assembled at the other end of the first slideway via a first fixing part and the two first belt wheels are arranged oppositely, and the first conveyor belt is arranged on the two first belt wheels in a sleeving manner and is located above a center line of the first slide rail; and wherein one of the first slideway and the second slideway is fixed to an upper portion of the first conveyor belt and the other one is fixed to a lower portion of the first conveyor belt, such that during a process where the first driving body drives the first conveyor belt to rotate, the first conveyor belt drives the first sliding seat and the second sliding seat to move close to each other or far away from each other.

Further, preferably, the medicine spraying apparatus includes a medicine spraying mechanism and a second driving mechanism that drives the medicine spraying mechanism to operate;

the medicine spraying mechanism includes a third sliding seat, a supporting rack, a spraying part, a spraying driving part and a liquid storage device;

the third sliding seat is slidably connected to the second slide rail, the supporting rack is assembled on the third sliding seat, the spraying part is assembled on the supporting rack and is used for spraying a medicine to a surface layer of the to-be-processed medicated thread, the spraying driving part is assembled on the supporting rack, is in signal connection and/or electrical connection to the control apparatus and is used for controlling and driving the spraying part to operate, and the liquid storage device is assembled on the supporting rack and/or the third sliding seat, is located directly below a spraying port of the spraying part and is used for collecting a residual liquid; and the second driving mechanism includes a second driving body, two second belt wheels and a second conveyor belt;

the second driving body is assembled at one end of the first slideway and is in signal connection and/or electrical connection to the control apparatus, one second belt wheel is assembled at the driving end of the second driving body and corresponds to a position of the second slide rail, the other second belt wheel is assembled at the other end of the second slideway via a second fixing part and the two second belt wheels are arranged oppositely, and the second conveyor belt is arranged on the two second belt wheels in a sleeving manner and is located above a center line of the second slide rail; and wherein the third sliding seat is fixed to the second conveyor belt, such that during a process where the second driving body drives the second conveyor belt to rotate, and the second conveyor belt drives the medicine spraying mechanism to move back and forth along the second slide rail so as to further spray the medicine to the surface layer of the to-be-processed medicated thread in the straightened state.

Further, preferably, the thread winding apparatus includes a thread winding mechanism and a third driving mechanism that drives the thread winding mechanism to operate;

the thread winding mechanism includes a fourth sliding seat, a thread winding seat and a second driving part, the fourth sliding seat is slidably connected to the second slideway, the second driving part is in signal connection and/or electrical connection to the control apparatus and is assembled on the fourth slide rail, and the thread winding seat is assembled at a driving end of the second driving part;

the third driving mechanism includes a third driving body, two third belt wheels and a third conveyor belt, the third driving body is assembled at the end, opposite to the first slideway, of the second slideway and is in signal connection and/or electrical connection to the control apparatus, one third belt wheel is assembled at the driving end of the third driving body and the other second belt wheel is assembled at the other end of the second slideway via a third fixing part and the two second belt wheels are arranged oppositely, and the third conveyor belt is arranged on the two third belt wheels in a sleeving manner and is located above a center line of the second slide rail; and wherein the fourth sliding seat is fixed to the third conveyor belt, during a process where the third driving body drives the third conveyor belt to rotate, the third conveyor belt drives the fourth sliding seat to move back and forth along the second slideway, such that the thread winding seat abuts a center position of the to-be-processed medicated thread in the single-strand rope state and the to-be-processed medicated thread is pulled toward a direction opposite to the first slideway to fold the to-be-processed medicated thread, and the second driving part drives the thread winding seat to rotate so as to further drive the to-be-processed medicated thread to rotate, such that the to-be-processed medicated thread winds and extends from middle to two ends to be twisted in a double-strand rope state.

Further, preferably, the thread winding seat includes a thread winding body and a winding hook assembly;

the thread winding body is assembled at the driving end of the second driving part, the winding hook assembly is elastically assembled at an end, opposite to the second driving part, of the thread winding body, the winding hook assembly moves toward the first slideway under the action of a tensile force and is restored to an initial position under the action of an elastic force after the tensile force is canceled; and wherein the winding hook assembly is used for abutting the center position of the to-be-processed medicated thread in the single-strand rope state and used for pulling the to-be-processed medicated thread along a direction opposite to the first slideway when being driven by the third driving mechanism, such that the to-be-processed medicated thread is folded; and the second driving part drives the thread winding body and the winding hook assembly to rotate, such that the to-be-processed medicated thread winds and extends from middle to two ends to be twisted in the double-strand rope state.

The present invention further provides a medicated thread manufacturing method for the medicated thread manufacturing system, the method including:

clamping two ends of a to-be-processed medicated thread to the thread clamping apparatus;

controlling, by the control apparatus, the thread clamping apparatus to straighten the to-be-processed medicated thread;

controlling, by the control apparatus, the medicine spraying apparatus to spray a medicine toward a surface layer of the to-be-processed medicated thread in the straightened state;

controlling, by the control apparatus, the thread clamping apparatus again to twist the to-be-processed medicated thread sprayed with the medicine into the single-strand rope state; and controlling, by the control apparatus, the thread winding apparatus to abut a center position of the to-be-processed medicated thread in the single-strand rope state and pull the to-be-processed medicated thread toward a direction opposite to the first slideway to fold the to-be-processed medicated thread, such that the to-be-processed medicated thread is driven to rotate, and therefore, the to-be-processed medicated thread winds and extends from middle to two ends to be twisted in the double-strand rope state.

The present invention has the beneficial effects that

1. In the patient, the thread clamping apparatus is controlled by the control apparatus to straighten the to-be-processed medicated thread, such that the to-be-processed medicated thread is in a tightened state, and it is convenient to spray the medicine to the surface layer thereof by the medicine spraying apparatus, such that the medicine can be attached to all areas in the surface layer of the to-be-processed medicated thread. If the to-be-processed medicated thread is in a bended state, a wrinkle area appears. When the medicine is sprayed, the wrinkle area cannot be covered with the medicine, such that the using effect is not good enough.

2. In the patent, the thread winding apparatus is controlled by the control apparatus again to twist the to-be-processed medicated thread sprayed with the medicine into the single-strand rope state, such that the medicated thread in the single-strand rope state is not only covered with the medicine in the surface layer, but also contains the medicine insides, and therefore, the content of the medicine is improved. Thus, in the contact process of the medicated thread and a human body, a function of the medicine can be exerted fully.

3. In the patent, the thread winding apparatus is further controlled to pull the to-be-processed medicated thread, such that the to-be-processed medicated thread is folded to further drive the to-be-processed medicated thread to rotate, and therefore, the to-be-processed medicated thread winds and extends from middle to two ends to be twisted into the double-strand rope state. During a process, the to-be-processed medicated thread is in the tightened state all the time, such that a condition that the to-be-processed medicated thread is floppy in the twisting process is avoided effectively, and therefore, every part thereof is stressed uniformly, thereby meeting a clinical demand.

4. In the patent, the control apparatus further can control strokes of the thread clamping apparatus, the medicine spraying apparatus and the thread winding apparatus, such that it can be further used for manufacturing medicated threads with different lengths and thicknesses, thereby meeting the clinical demands of different patients. The patient can adjust the dimension of the medicated thread flexibly according to an actual need, such that the applicable scene of the application is improved greatly.

5. In the patent, in the whole course of manufacturing the medicated thread by the medicated thread manufacturing system, artificial participation is not needed, such that the cleanliness and efficiency of the medicated thread product are improved greatly.

6. In the patent, the first slideway and the second slideway are arranged in T shape, such that it is convenient to match the thread clamping apparatus, the medicine spraying apparatus and the thread winding apparatus.

7. In the patent, the medicated thread manufacturing system is small in size, light in weight and convenient for the patient himself or herself to carry and twist the medicated thread, such that a lot of cost for purchasing the medicated thread is saved. The medicated thread can be manufactured and used on site, such that a condition that infection of the wound is aggravated as the medicated thread placed for a long time is contaminated by bacteria and stains is avoided.

BRIEF DESCRIPTION OF THE DRAWINGS

Further description of the present invention will be made below in combination with drawings and specific embodiments.

DESCRIPTION OF MARKS OF DRAWINGS

100, thread clamping apparatus; 110, first thread clamping mechanism; 111, first sliding seat; 1111, sliding wheel; 1112, supporting plate; 1113, fastener; 112, first clamping seat; 1121, first clamping body; 11211, first leaning block; 11212, second leaning block; 11213, connecting piece; 1122, first clamping head; 11221, clamping head body; 11222, fastening rotary knob; 11223, slide bar; 11224, spring; 11225, first limiting block; 11226, second limiting block; 113, first driving part; 120, second clamping mechanism; 121, second sliding seat; 122, second clamping seat; 1221, second clamping body; 1222, second clamping head; 130, first driving mechanism; 131, first driving body; 132, first belt wheel; 133, first conveyor belt; 134, first fixing part;

200, medicine spraying apparatus; 210, medicine spraying mechanism; 211, third sliding seat; 212, supporting rack; 2121, bottom; 2122, side portion; 2123, top; 21231, free end; 2124, driving part mounting portion; 213, spray part; 2131, liquid storage body; 2132, first medicine conveying pipe; 2133, spray head; 2134, second medicine conveying pipe; 214, driving part; 215, liquid storage device; 220, second driving mechanism; 221, second driving body; 222, second belt wheel; 223, second conveyor belt; 224, second fixing part;

300, thread winding apparatus; 310, thread winding mechanism; 311, fourth sliding seat; 312, thread winding seat; 3121, thread winding body; 3122, winding hook assembly; 31221, winding hook; 313, second driving part; 320, third driving mechanism; 321, third driving body; 322, third belt wheel; 323, third conveyor belt; 324, third fixing part;

400, control apparatus; 410, control box; 411, display screen; 412, rotary knob; 413, zeroing button; 414, start button;

510, first slideway; 511, first slide rail; 5111, sliding wheel accommodation groove; 512, second slide rail; 520, second slideway;

610, worktable; 620, guide wire.

DETAILED DESCRIPTION OF THE EMBODIMENTS

In order to more clearly describe the technical solutions in the embodiments of the present invention or in the prior art, the drawings to be used in the description of the embodiments or the prior art will be briefly introduced hereafter. It would be obvious that the drawings described below are only some embodiments of the present invention, and a person skilled in the art could obtain other drawings according to these accompanying drawings without involving an inventive effort.

According to a specific embodiment provided by the present invention, as shown in FIG. 1 to FIG. 4, a medicated thread manufacturing system includes a first slideway 510 and a second slideway 520 arranged in T shape, a thread clamping apparatus 100 and a medicine spraying apparatus 200 slidably arranged on the first slideway 510 and a thread winding apparatus 300 slidably arranged on the second slideway 520. The thread clamping apparatus 100 is used for clamping two ends of a to-be-processed medicated thread, straightening the to-be-processed medicated thread and twisting the to-be-processed medicated thread in the straightened state into a single-strand rope state. The medicine spraying apparatus 200 is used for spraying a medicine towards a surface layer of the to-be-processed medicated thread in the straightened state. The thread winding apparatus 300 is used for abutting a center position of the to-be-processed medicated thread in the single-strand rope state and pulling the to-be-processed medicated thread towards a direction opposite to the first slideway 510, such that the to-be-processed medicated thread is folded. The to-be-processed medicated thread is rotated, such that the to-be-processed medicated thread winds and extends from middle to two ends to be twisted in a double-strand rope state. The control apparatus 400 in signal connection and/or electrical connection with the thread clamping apparatus 100, the medicine spraying apparatus 200 and the thread winding apparatus 300 to control a matching opportunity of the thread clamping apparatus 100, the medicine spraying apparatus 200 and the thread winding apparatus 300.

In the embodiment, the first slideway 510 and the second slideway 520 are arranged in T shape, such that it is convenient to match the thread clamping apparatus 100, the medicine spraying apparatus 200 and the thread winding apparatus 300. The thread clamping apparatus 100 is controlled by the control apparatus 400 to straighten the to-be-processed medicated thread, such that the to-be-processed medicated thread is in a tightened state, and it is convenient to spray the medicine to the surface layer thereof by the medicine spraying apparatus 200, such that the medicine can be attached to all areas in the surface layer of the to-be-processed medicated thread. If the to-be-processed medicated thread is in a bended state, a wrinkle area appears. When the medicine is sprayed, the wrinkle area cannot be covered with the medicine, such that the using effect is not good enough. The thread winding apparatus 100 is controlled by the control apparatus 400 again to twist the to-be-processed medicated thread sprayed with the medicine into the single-strand rope state, and the thread winding apparatus 300 is further controlled to pull the to-be-processed medicated thread, such that the to-be-processed medicated thread is folded to further drive the to-be-processed medicated thread to rotate, and therefore, the to-be-processed medicated thread winds and extends from middle to two ends to be twisted into the double-strand rope state. In the process, the to-be-processed medicated thread is in the tightened state all the time, such that a condition that the to-be-processed medicated thread is floppy in the twisting process is avoided effectively, and therefore, every part thereof is stressed uniformly, thereby meeting a clinical demand. The control apparatus 400 further can control strokes of the thread clamping apparatus 100, the medicine spraying apparatus 200 and the thread winding apparatus 300, such that it can be further used for manufacturing medicated threads with different lengths and thicknesses, thereby meeting the clinical demands of different patients. According to the patent, in the process of manufacturing the medicated thread, artificial participation is not needed, such that the cleanliness of the medicated thread product is improved greatly.

Figure 3:
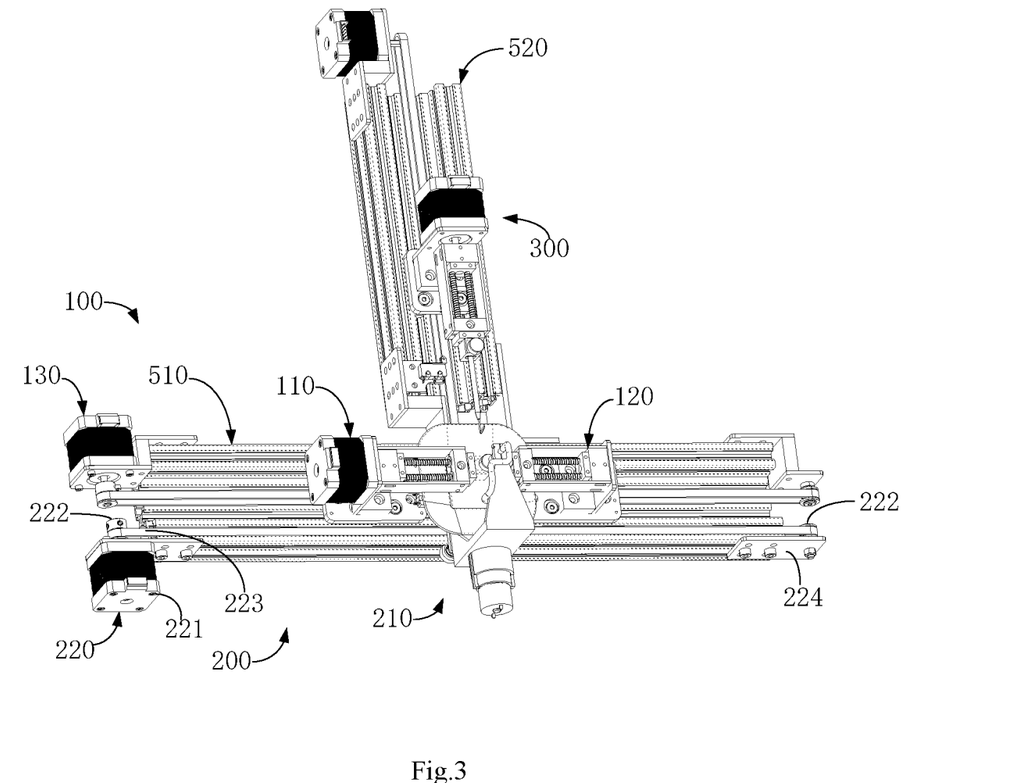
FIG. 3 is a position structural schematic diagram of the thread clamping apparatus, the medicine spraying apparatus and the thread winding apparatus shown in the FIG. 2.
Figure 4:
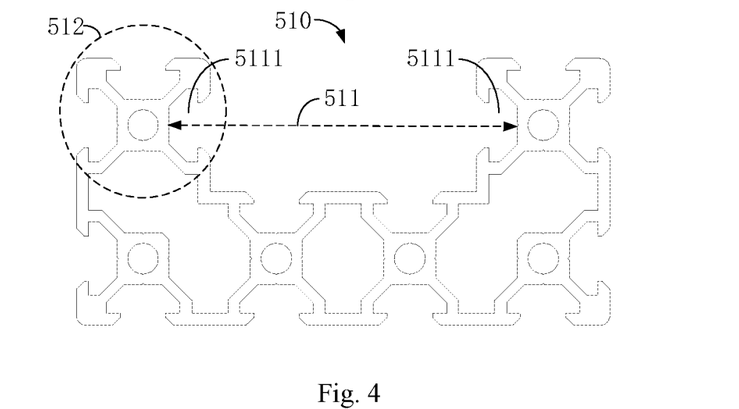
FIG. 4 is a cross-section view of the first slideway shown in the FIG. 3.

In the embodiment, referring to FIG. 3 and FIG. 4, the first slideway 510 and the second slideway 520 can be manufactured by an aluminum alloy profile or a lightgage steel joist profile, such that it can be ensured that the slideways have better bearing capacities and do not bring overburden, such that it is convenient to transport and carry. Preferably, the second slideway 520 is perpendicular to the first slideway 510 and abuts against a middle position of the first slideway 510, and a connection of the two can be fixed via a metal sheet matched with a screw, which is not limited herein.

Figure 1:
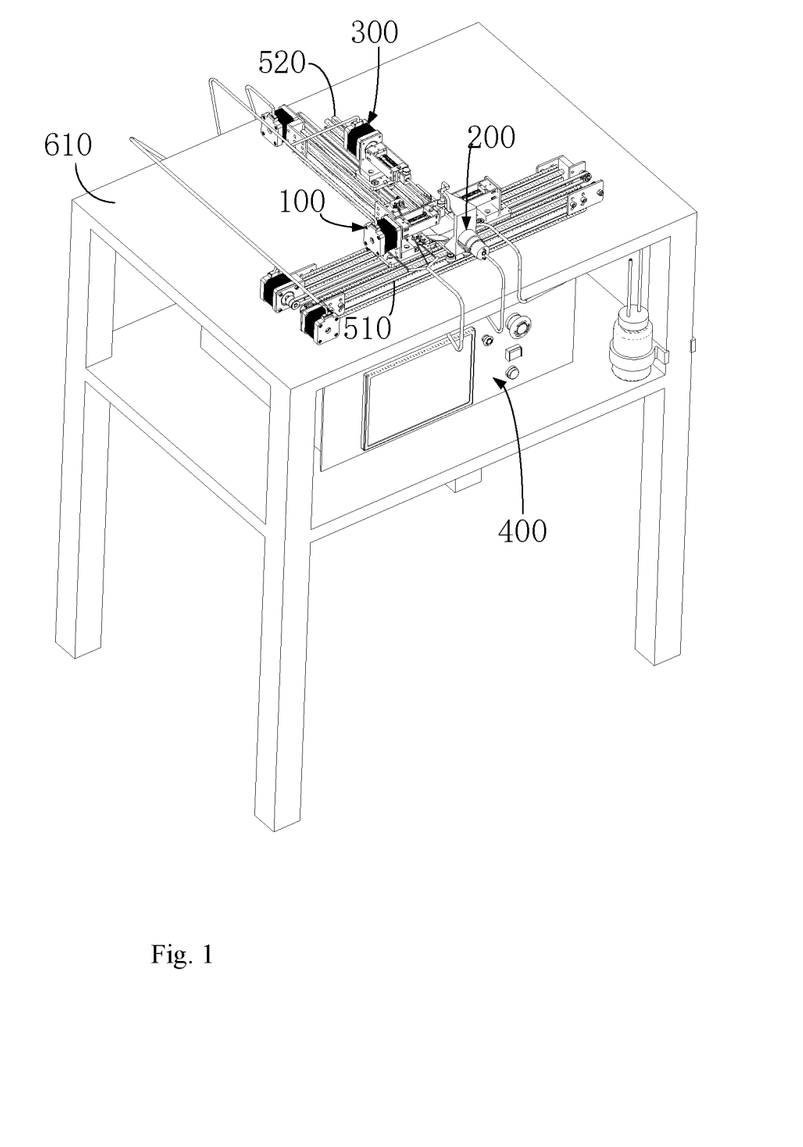
FIG. 1 is a structural schematic diagram of a product assembled on a worktable of the present invention.

In the embodiment, referring to FIG. 1, in order for user's operation, the patent can be assembled on the worktable 610. As the table board of the worktable 610 is flat, the first slideway 510 and the second slideway 520 are in a horizontal state or an approximately horizontal state all the way. Thus, in the process of manufacturing the medicated thread, a condition that the medicated threaded manufacturing system inclined locally as the table board or a bearing surface is uneven is avoided, such that the quality of the medicated threaded product is further affected. In a preferred example, referring to FIG. 1, the worktable 610 is internally provided with a storage space for storing the control apparatus 400, such that the control apparatus 400 is not contacted with the rest of apparatuses, thereby, on the one hand, facilitating user's operation and on the other hand, preventing the control apparatus 400 from being damaged as an emergency situation in an operating process happens.

Figure 2:
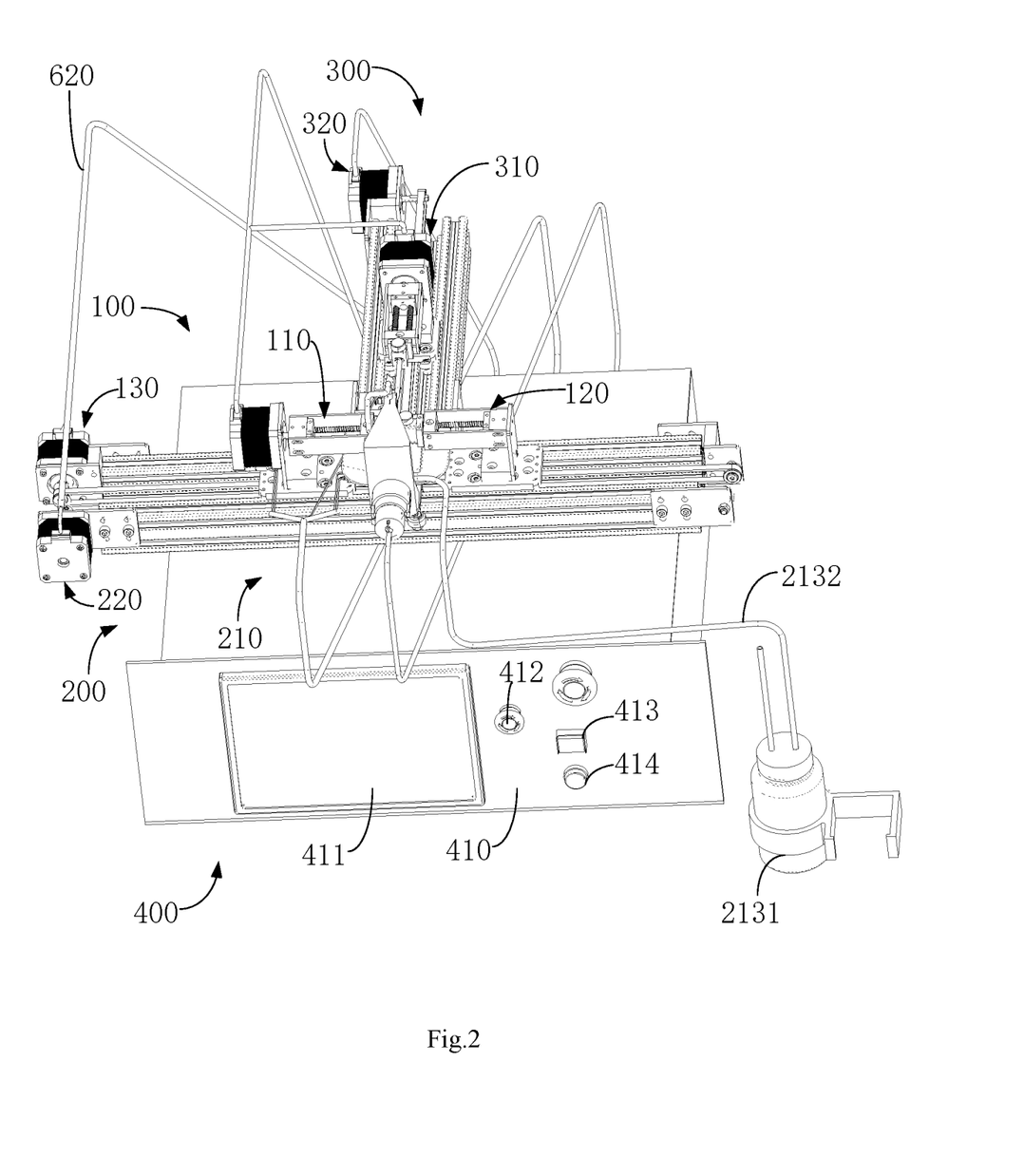
FIG. 2 is a three-dimensional structural schematic diagram of the product of the present invention.

In the embodiment, referring to FIG. 2 to FIG. 4, both the thread clamping apparatus 100 and the medicine spraying apparatus 200 are slidably arranged on the first slideway 510. The thread clamping apparatus 100 is controlled by the control apparatus 400 to straighten the to-be-processed medicated thread, such that the to-be-processed medicated thread is in a tightened state, and it is convenient to spray the medicine to the surface layer thereof by the medicine spraying apparatus 200, such that the medicine can be attached to all areas in the surface layer of the to-be-processed medicated thread. Thus, in order to ensure that the thread clamping apparatus 100 and the medicine spraying apparatus 200 can operate independently and one of the thread clamping apparatus and the medicine spraying apparatus is not hindered by the other one of the thread clamping apparatus and the medicine spraying apparatus in the operating process, preferably, the first slideway 510 is provided with the first slide rail 511 and the second slide rail 512 arranged parallelly, the thread clamping apparatus 100 is slidably arranged on the first slide rail 511 and the medicine spraying apparatus 200 is slidably arranged on the second slide rail 512. Certainly, in the embodiment, contour construction of the first slide rail 511 and the second slide rail 512 cannot be defined specifically and can changed flexibly according to actual application scenarios. As a preferred example, the second slide rail 512 is arranged on a side, opposite to the second slide way 520, of the first slideway 511. Thus, the thread winding apparatus 300 is not hindered by the medicine spraying apparatus 200 during a process where the thread winding apparatus is abutted with the to-be-processed medicated thread.

Figure 5:
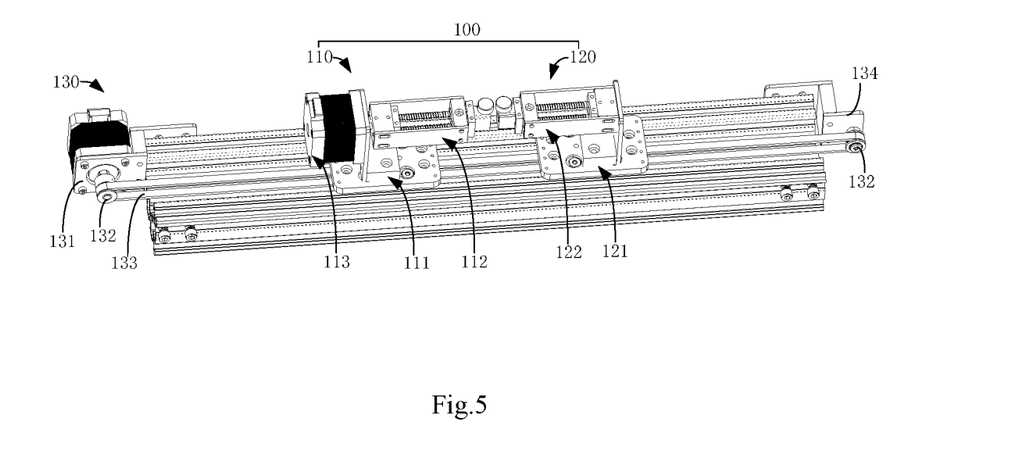
FIG. 5 is a three-dimensional structural schematic diagram of the thread clamping apparatus shown in the FIG. 3.

As a preferred scheme of the embodiment, referring to FIG. 5, the thread clamping apparatus 100 can include the first clamping mechanism 110, the second clamping mechanism 120 and the first driving mechanism 130. Specifically, both the first clamping mechanism 110 and the first driving mechanism 130 are in signal connection and/or electrical connection to the control apparatus 400. Both the first clamping mechanism 110 and the second clamping mechanism 120 are slidably connected with the first slide rail 511 and are respectively used for clamping two ends of the to-be-processed medicated thread. The first driving mechanism 130 is assembled at one end of the first slideway 510 and is used for driving the first clamping mechanism 110 and the second clamping mechanism 120 to move close to each other or far away from each other, wherein when the to-be-processed medicated thread is in the straightened state after the first clamping mechanism 110 and the second clamping mechanism 120 move in a deviated manner, the first clamping mechanism 110 is further used for twisting the to-be-processed medicated thread into the single-strand rope state.

Specifically, referring to FIG. 4 and FIG. 5, the first clamping mechanism 110 can include the first sliding seat 111, the first clamping seat 112 and the first driving part 113. The second clamping mechanism 120 can include the second sliding seat 121 and the second clamping seat 122. Both the first sliding seat 111 and the second sliding seat 121 are slidably connected with the first slide rail 511. The first driving part 113 is in signal connection and/or electrical connection with the control apparatus 400. Under control of the control apparatus 400, the first driving part drives the first clamping seat 112 to rotate to twist the to-be-processed medicated thread. The first driving part 113 can be a driving motor. The first driving part 113 is assembled on the first sliding seat 111 and a driving end thereof faces the second clamping mechanism 120, and a driving direction thereof is parallel to the first slide rail 511. The first clamping seat 112 is assembled at the driving end of the first driving part 113. The second clamping seat 122 is assembled on the second sliding seat 121 and is arranged opposite to the first clamping seat 112. The first clamping seat 112 and the second clamping seat 122 are used for clamping two ends of the to-be-processed medicated thread respectively, and when the to-be-processed medicated thread is in the straightened state, the first driving part 113 drives the first clamping seat 112, the second clamping seat 122 is fixedly arranged, that is, when the to-be-processed medicated thread is in the straightened state, one end of the to-be-processed medicated thread is fixed while the other end of the to-be-processed medicated thread is started to be twisted, thereby forming the single-strand rope state finally.

Figure 6:
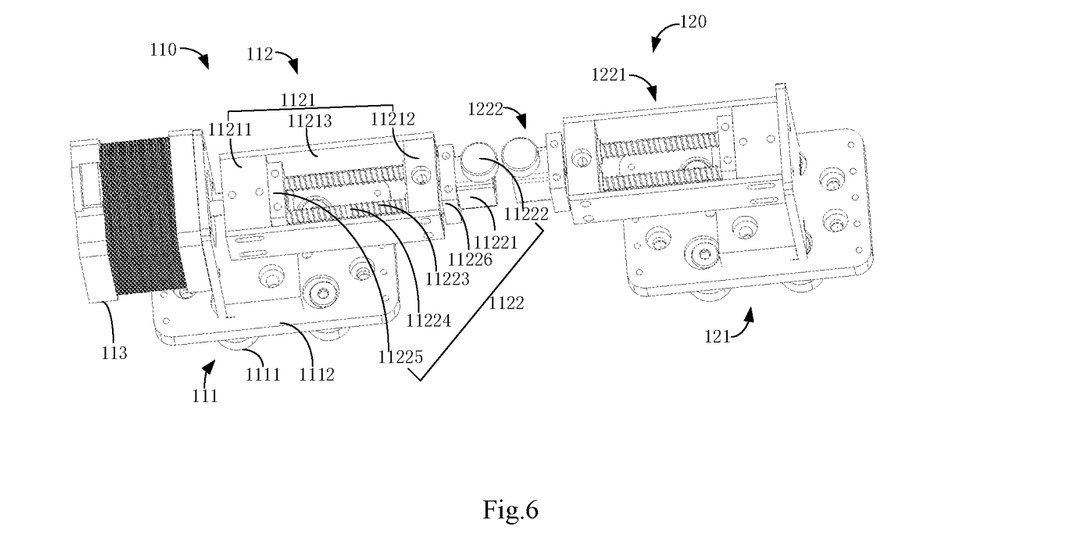
FIG. 6 is a position structural schematic diagram of the first clamping mechanism and the second clamping mechanism shown in the FIG. 5.

Further preferably in the embodiment, referring to FIG. 6, the first sliding seat 111 can include the supporting plate 1112 and the sliding wheel 1111. Specifically, the supporting plate 1112 is used for bearing and fixing the first driving part 113, and the quantity of the sliding wheels 1111 is preferably four and the sliding wheels are respectively arranged at four corners of the bottom 2121 of the supporting plate 1112. In a preferred application scene, referring to FIG. 4, the first slide rail 511 is approximately groove shaped, two inner side surfaces of the first slide rail 511 are respectively provided with concave sliding wheel accommodation grooves 5111, and the sliding wheel accommodation grooves 5111 extend to two ends of a length direction of the first slide rail 511. The two sliding wheels 1111 located above the same side of the supporting plate 1112 are assembled in one sliding wheel accommodation groove 5111, the two sliding wheels 1111 located above the other side of the supporting plate 1112 are assembled in the other sliding wheel accommodation groove 5111, the supporting plate 1112 is located right above the first slide rail 511, and under the limiting action of the four sliding wheels 1111, the supporting plate 1112 is not contacted with the upper end surface of the first slide rail 511. Thus, the first sliding seat 111 can move back and forth smoothly along the length direction of the first slide rail 511 to further drive the first supporting seat 112 and the first driving part 113 to move back and forth along the length direction of the first slide rail 511.

Consistently, the specific contour construction of the second sliding seat 121 is consistent with that of the first sliding seat 111 and can be referred to specific description about the first sliding seat 111, which is no longer repeatedly described.

Further, referring to FIG. 5, the first driving mechanism 130 can include the first driving body 131, two first belt wheels 132 and the first conveyor belt 133; The first driving body 131 can be the driving motor, is assembled at one end of the first slideway 510 and is in signal connection and/or electrical connection to the control apparatus 400. One first belt wheel 132 is assembled at the driving end of the first driving body 131, and the first belt wheel 132 corresponds to an end portion position of the first slide rail 511. The other first belt wheel 132 is assembled at the other end of the first slideway 510 via one first fixing part 134 and the two first belt wheels 132 are arranged oppositely. The first conveyor belt 133 is arranged on the two first belt wheels 132 in a sleeving manner and is located above the center line of the first slide rail 511. The first conveyor belt 133 is of an annular structure and is arranged vertically, one of the supporting plate 1112 of the first sliding seat 111 and the supporting plate of the second sliding seat 121 is fixed to the upper portion of the first conveyor belt 133 while the other one is fixed to the lower portion of the first conveyor belt 133. Controlled by the control apparatus 400, during a process where the first driving body 131 drives the first conveyor belt 133 to rotate, the moving directions of the upper portion and the lower portion are opposite, such that the first conveyor belt 133 drives the first sliding seat 111 and the second sliding seat 121 to move close to each other or far away from each other.

Figure 7:
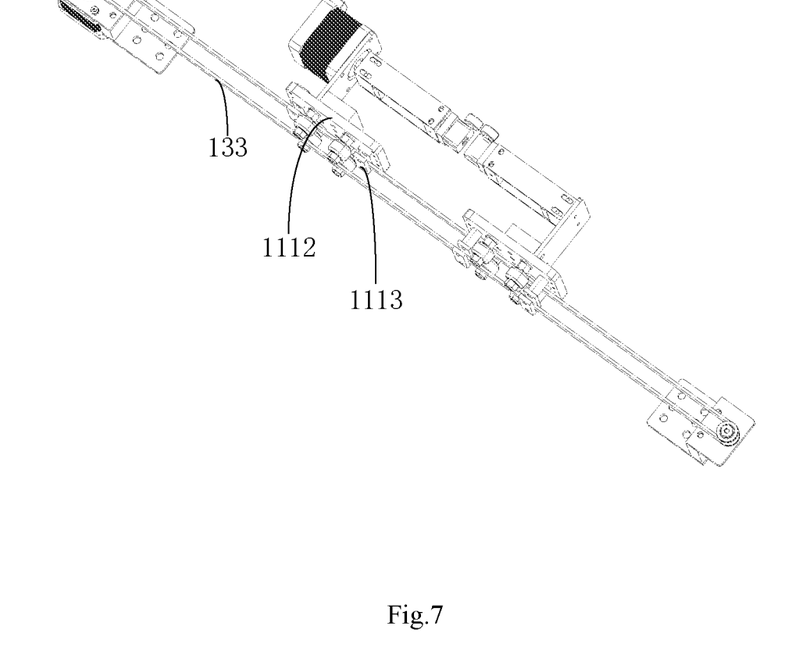
FIG. 7 is a structural schematic diagram in which the first sliding seat and the second sliding seat shown in the FIG. 5 are fixed to the first conveyor belt respectively.

As a preferred example of the embodiment, referring to FIG. 7, the bottom of the supporting plate 1112 of the first sliding seat 111 is attached to the upper portion of the first conveyor belt 133 and is fixed and abutted to the first conveyor belt 133 via a fastener 1113, wherein the fastener 1113 can be of a sheety or blocky structure which can lock the first conveyor belt 133 to the bottom of the supporting plate 1112 via a screw, but it is not limited to this. Correspondingly, the bottom of the supporting plate of the second sliding seat 121 is attached to the lower portion of the first conveyor belt 133 and is fixed and abutted to the first conveyor belt 133 via a fastener, and the fixing mode is consistent with the above mode, which is no longer described repeatedly herein. Certainly, as another example, the bottom of the supporting plate 1112 of the first sliding seat 111 can be further attached to the lower portion of the first conveyor belt 133, and the bottom of the supporting plate of the second sliding seat 121 can be further attached to the upper portion of the first conveyor belt 133, which can also achieve the same effect.

It is worth mentioning that it should be ensured that the positions where the first sliding seat 111 and the second sliding seat 121 are assembled on the first conveyor belt 133 are symmetrical relative to the second slideway 520. Thus, it is convenient for the thread winding apparatus 300 to abut a center position of the to-be-processed medicated thread in the single-strand rope state.

Further preferably in the embodiment, referring to FIG. 6, the first clamping seat 112 can include the clamping body 1121 and the first clamping head 1122. The first clamping body 1121 is assembled at the driving end of the first driving part 113, the first clamping head 1122 is elastically assembled at an end, opposite to the first driving part 113, of the first clamping body 1121, the first clamping head 1122 is used for clamping one end of the to-be-processed medicated thread, and moves towards the second clamping seat 122 under the action of a tensile force of the to-be-processed medicated thread and is restored to an initial position under the action of an elastic force after the tensile force is canceled. The second clamping mechanism 122 includes a second clamping body 1221 and a second clamping head 1222. The second clamping body 1221 is assembled on the second sliding seat 121, the second clamping head 1222 is elastically assembled at an end, facing the first clamping body 1121, of the second clamping body 1221, the second clamping head 1222 is used for clamping the other end of the to-be-processed medicated thread, and moves towards the first clamping seat 112 under the action of a tensile force of the to-be-processed medicated thread and is restored to the initial position under the action of the elastic force after the tensile force is canceled. During a process where the to-be-processed medicated thread in the straightened state is twisted into the single-strand rope state, a length thereof is shortened gradually, and the first clamping head 1122 and the second clamping head 1222 provide an elastic force for keeping the to-be-processed medicated thread tight.

As a preferred example of the embodiment, referring to FIG. 6, the first clamping body 1121 can include the first leaning block 11211, the second leaning block 11212 and two connecting sheets 11213. The first leaning block 11211 and the second leaning block 11212 are equal in width, the first leaning block 11211 is assembled at the driving end of the first driving part 113, the second leaning block 11212 and the first leaning block 11211 are opposite to each other, are arranged at a certain interval, and are fixed via the two connecting sheets 11213 and the first leaning block 11211 to form a hollow square frame structure.

Correspondingly, referring to FIG. 6, the first clamping head 1122 can include the clamping head body 11221, the fastening rotary knob 11222, the first limiting block 11225, the second limiting block 11226, two slide bars 11223 and two springs 11224. Specifically, two symmetrical slide holes are formed along a width direction of the second leaning block 11212, the two slide bars 11223 are respectively inserted into the two slide holes, such that one ends of the two slide barfs 11223 extend into the first clamping body 1121, the two springs 11224 are respectively arranged on parts, extending into the first clamping body 1121, of the two slide bars 11223 in a sleeving manner, the first limiting block 11225 is fixed to the ends, extending into the first clamping body 1121, of the two slide bars 11223, and on the one hand, the first limiting block 11225 plays a role of fixing the springs 11224 to enable the springs 11224 to have elastic forces, and on the other hand, the first limiting block can further be used for leaning the second leaning block 11212 to prevent the two slide bars 11223 from spranging, such that the two slide bars 11223 only can move back and forth in a special range. The second limiting block 11226 is located outside the first clamping body 1121 and is matched with the second leaning block 11212 and is used for fixing the ends, opposite to the first limiting block 11225, of the two slide bars 11223, and the ends, opposite to the second leaning block 11212, of the second limiting block 11226 is further used for fixing the clamping head body 11221. The end, facing the second clamping mechanism 120, of the clamping head body 11221 is provided with a medicated thread mounting hole for mounting an end portion of the medicated thread, a side portion 2122 of the clamping head body 11221 is further provided with a fastening hole perpendicular to the medicated thread mounting hole. The fastening rotary knob 11222 can screw into the fastening hole to fix the end portion of the medicated thread.

It is worth mentioning that further referring to FIG. 6, the specific contour constructions of the second clamping body 1221 and the second clamping head 1222 are as same as those of the first clamping body 1121 and the first clamping head 1122. The specific contour constructions specifically refer to the description above, which is no longer described repeatedly herein.

It is worth mentioning that during a process where the to-be-processed medicated thread in the straightened state is twisted into the single-strand rope state, a length thereof is shortened gradually, and the first clamping seat 112 and the second clamping seat 122 are kept unchanged in position as the to-be-processed medicated thread is in the tightened state. In order to ensure that the to-be-processed medicated thread is not snapped rigidly during a process where the to-be-processed medicated thread is shortened in length effectively, elastic movement of the first clamping head 1122 and the second clamping head 1222 can provide an elastic force for keeping the to-be-processed medicated thread tight.

In the embodiment, the first clamping mechanism 110 and the second clamping mechanism 120 are controlled by the control apparatus 400 to straighten the to-be-processed medicated thread, such that the to-be-processed medicated thread is in a tightened state, and it is convenient to spray the medicine to the surface layer thereof by the medicine spraying apparatus 200, such that the medicine can be attached to all areas in the surface layer of the to-be-processed medicated thread. If the to-be-processed medicated thread is in a bended state, a part of wrinkle area appears. When the medicine is sprayed, the wrinkle area cannot be covered with the medicine, such that the using effect is not good enough. The medicine spraying apparatus 200 sprays the medicine before the to-be-processed medicated thread is twisted into the single-strand rope state. Thus, the thread winding apparatus 100 is controlled by the control apparatus 400 again to twist the to-be-processed medicated thread sprayed with the medicine into the single-strand rope state, such that the medicated thread in the single-strand rope state is not only covered with the medicine in the surface layer, but also contains the medicine insides, and therefore, the content of the medicine is improved. Thus, in the contact process of the medicated thread and a human body, a function of the medicine can be exerted fully.

It is worth mentioning that in the patient, the type of the medicine sprayed by the spraying apparatus 200 is not limited, which may be any needed type of medicine, and therefore, patients of various types can use the medicine properly. For example, the medicine may be alcohol, an anti-inflammatory drug or a painkiller, which is not limited herein. The patient can replace the medicine arbitrarily according to an actual using demand.

As a preferred scheme of the embodiment, referring to FIG. 2, FIG. 3, FIG. 8 and FIG. 9, the medicine spraying apparatus 200 can include the medicine spraying mechanism 210 and the second driving mechanism 220 that drives the medicine spraying mechanism 210 to operate.

Figure 8:
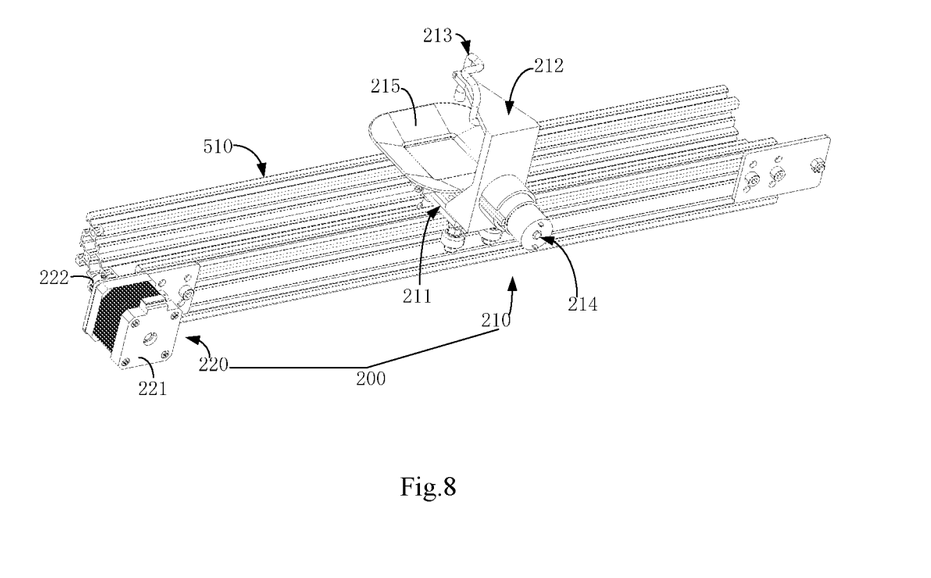
FIG. 8 is a three-dimensional structural schematic diagram of the medicine spraying apparatus shown in the FIG. 3.

Specifically, referring to FIG. 2 and FIG. 8, the medicine spraying mechanism 210 can include the third sliding seat 211, the supporting rack 212, the spraying part 213, the spraying driving part 214 and the liquid storage device 215. The third sliding seat 211 is slidably connected with the second slide rail 512. The specific contour construction of the third sliding seat 211 is consistent with that of the first sliding seat 111 and the second sliding seat 121 and can be referred to specific description about the first sliding seat 111, which is no longer repeatedly described. Referring to FIG. 4, the left and right sides of the second slide rail 512 are further provided with sliding wheel accommodation grooves for four sliding wheels of the third sliding seat 211 to slide, which specifically refers to a sliding mode of the sliding wheel 1111 of the first sliding seat 111. Further, for the sake of attractiveness of the design, the structures of the thread clamping apparatus 100 and the medicine spraying apparatus 200 are more compact, and a connection between the second slide rail 512 and the first slide rail 511 share the same sliding wheel accommodation groove, which is not limited herein.

Figure 9:
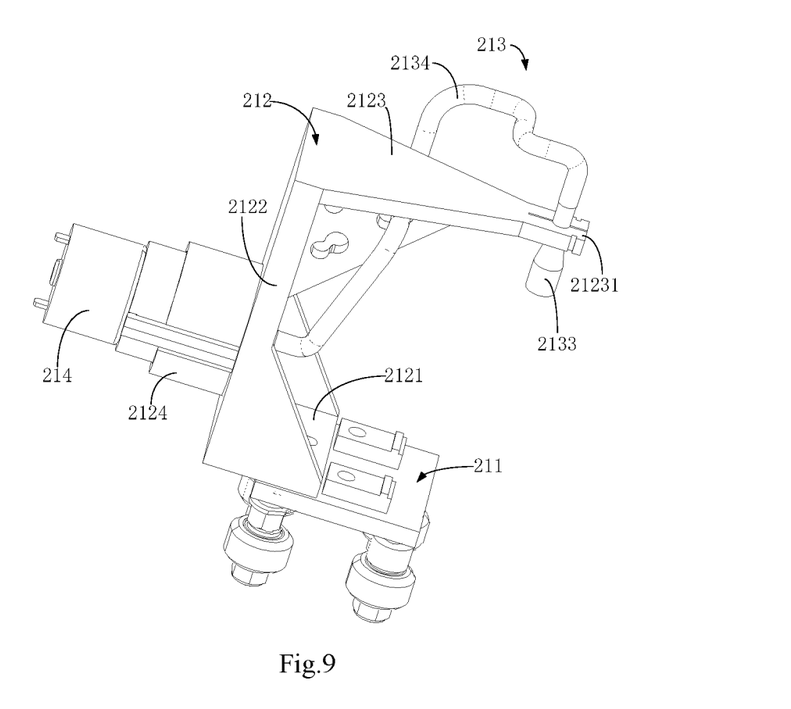
FIG. 9 is a three-dimensional structural schematic diagram of the medicine spraying apparatus shown in the FIG. 8.

Further, referring to FIG. 9, the supporting rack 212 is assembled on the third sliding seat 211. The spraying part 213 is assembled on the supporting rack 212 and is used for spraying a medicine to a surface layer of the to-be-processed medicated thread. The spraying driving part 214 is assembled on the supporting rack 212 and is in signal connection and/or electrical connection with the control apparatus 400. Under control of the control apparatus 400, the spraying driving part is used for controlling and driving the spraying part 213 to spray the medicine. The liquid storage device 215 is assembled on the supporting rack 212 and/or the third sliding seat 211 and is located directly below the spraying port of the spraying part 213 for collecting a residual liquid.

Specifically, referring to FIG. 1 to FIG. 3 and FIG. 9, the supporting rack 212 can include the bottom 2121, the side portion 2122 and the top 2123. The bottom 2121 and the top 2123 are arranged in parallel, and the side portion 2122 is connected with the bottom 2121 and the top 2123 and is located on one side of the top 2123 and the bottom 2121. The bottom 2121 is used for fixing the third sliding seat 211, the top 2123 extends towards the direction of the to-be-processed medicated thread, and the free end 21231 of the top 2123 is aligned with the position right above the to-be-processed medicated thread. The side, opposite to the to-be-processed medicated thread, of the side portion 2122 is provided with the driving part mounting portion 2124 for mounting the spraying driving part 214. The spraying part 213 can include the liquid storage body 2131, the first medicine conveying pipe 2132, the second medicine conveying pipe 2134 and the spraying head 2133. The liquid storage body 2131 is used for storing a liquid medicine, and its mounting position is not limited. For example, referring to FIG. 1 and FIG. 2, it can be mounted in the storage space of the worktable 610 and is not limited herein. The liquid storage body 2131 is communicated with the spraying driving part 214 via the first medicine conveying pipe 2132 and the spraying driving part 214 is communicated with the spraying head 2133 via the second medicine conveying pipe 2134. The spraying driving part 214 can be an injection motor. The liquid storage body 2131 conveys the liquid medicine to the spraying driving part 214 first, and then the spraying driving part 214 presses the liquid medicine into the spraying head 2133, such that the spraying head 2133 has enough power to be aligned with the to-be-processed medicated thread to spray the medicine. Preferably, the liquid medicine sprayed by the spraying head 2133 is vaporific, such that the surface layer of the to-be-processed medicated thread is covered with the medicine, and therefore, a condition of excessive more or less liquid medicine locally is avoided. Preferably, the spraying head 2133 can be assembled at the front end 21231 of the top 2123 of the supporting rack 212, that is, the top 2123 facing the direction of the to-be-processed medicated thread, such that the spraying head 2133 is just located in a position right above the to-be-processed medicated thread, and the way that the spraying head 2133 is assembled at the free end 21231 is not limited. As a preferred example, referring to FIG. 9, the free end 21231 can be made from an elastic or a slightly elastic material, a gap can be formed in a center position of the free end 21231, a mounting hole is formed in a middle position of the gap, and the spraying head 2133 is assembled in the mounting hole via the gap to be fixed. The mode is easy to operate and good in stability. The liquid storage device 215 is located directly below the spraying head 2133, and it is of a disc-shaped structure for collecting and recovering the liquid medicine left in the spraying head 2133.

Further, referring to FIG. 3, the second driving mechanism 220 can include the second driving body 221, two second belt wheels 222 and the second conveyor belt 223. The second driving body 221 is assembled at one end of the first slideway 510 and is in signal connection and/or electrical connection to the control apparatus 400. One of second belt wheels 222 is assembled at the driving end of the second driving body 221, and the second belt wheel 222 corresponds to an end portion position of the second slide rail 512. The other one of second belt wheels 222 is assembled at the other end of the second slideway 510 via one second fixing part 224 and the two second belt wheels 222 are arranged oppositely. The second conveyor belt 223 is arranged on the two second belt wheels 222 in a sleeving manner and is located above the center line of the second slide rail 512. The third sliding seat 211 is fixed to the second conveyor belt 223, such that during a process where the second driving body 221 drives the second conveyor belt 223 to rotate, and the second conveyor belt 223 drives the medicine spraying mechanism 210 to move back and forth along the second slide rail 512 so as to further spray the medicine to the surface layer of the to-be-processed medicated thread in the straightened state. The mode of fixing the third sliding seat 211 to the second conveyor belt 223 is as same as that of fixing the first sliding seat 111 to the first conveyor belt 133, which is no longer repeatedly described.

In the embodiment, referring to FIG. 1 to FIG. 3, and FIG. 10, the thread winding apparatus 300 can include the thread winding mechanism 310 and the third driving mechanism 320 that drives the thread winding mechanism 310 to operate. The thread winding mechanism 310 can include the fourth sliding seat 311, the thread winding seat 312 and the second driving part 313. The fourth sliding seat 311 is slidably connected with the second slideway 520. The second driving part 313 is in signal connection and/or electrical connection to the control apparatus 400 and is assembled on the fourth sliding seat 311, and the thread winding seat 312 is assembled at the driving end of the second driving part 313. The third driving mechanism 320 includes the third driving body 321, two third belt wheels 322 and the third conveyor belt 323.

Figure 10:
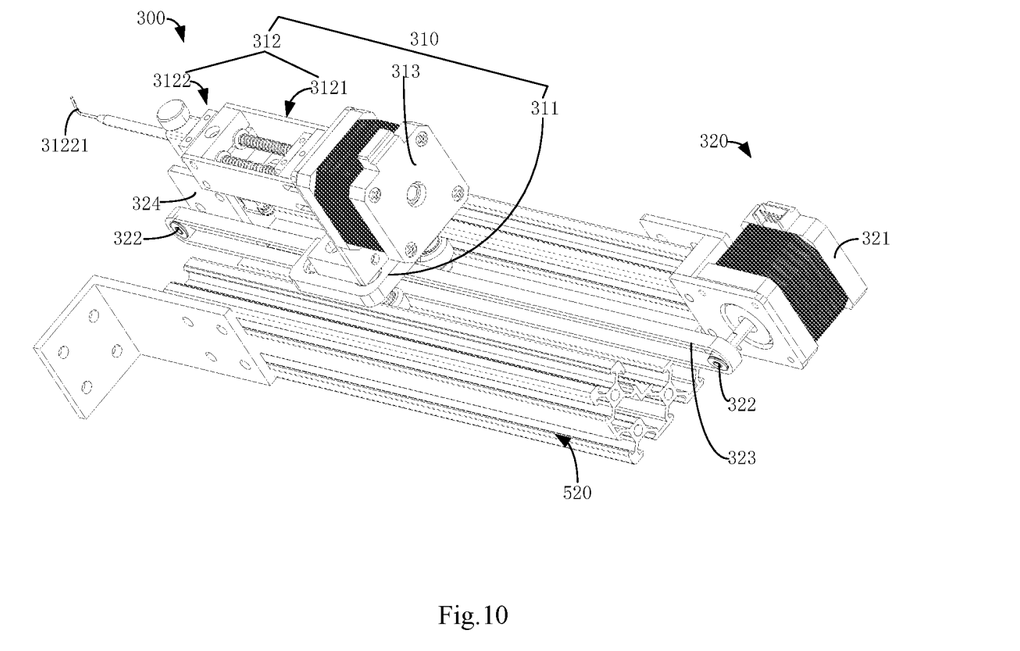
FIG. 10 is a three-dimensional structural schematic diagram of the thread winding apparatus shown in the FIG. 3.

The third driving body 321 is assembled at the end of the first slideway 510 opposite to the second slideway 520 and is in signal connection and/or electrical connection to the control apparatus 400. One of third belt wheels 322 is assembled at the driving end of the third driving body 321 while the other one of third belt wheels 322 is assembled at the other end of the second slideway 520 via a third fixing part 324, and the two third belt wheels 322 are arranged oppositely. The third conveyor belt 323 is arranged on the two third belt wheels 322 in a sleeving manner and is located above the center line of the second slideway 520. The fourth sliding seat 311 is fixed to the third conveyor belt 323, during a process where the third driving body 321 drives the third conveyor belt 323 to rotate, the third conveyor belt 323 drives the fourth sliding seat 311 to move back and forth along the second slideway 520, such that the thread winding seat 312 abuts a center position of the to-be-processed medicated thread in the single-strand rope state and pulling the to-be-processed medicated thread towards a direction opposite to the first slideway 510, and therefore, the to-be-processed medicated thread is folded; the second driving part 313 drives the thread winding seat 312 to rotate so as to further drive the to-be-processed medicated thread to rotate, such that the to-be-processed medicated thread winds and extends from middle to two ends to be twisted in a double-strand rope state.

Further preferably in the embodiment, the thread winding seat 312 can include the thread winding body 3121 and the winding hook assembly 3122. The thread winding body 3121 is assembled at the driving end of the second driving part 313, the winding hook assembly 3122 is elastically assembled at an end, opposite to the second driving part 313, of the thread winding body 3121, the winding hook assembly 3122 moves toward the first slideway 510 under the action of a tensile force and is restored to an initial position under the action of an elastic force after the tensile force is canceled. The winding hook assembly 3122 is used for abutting the center position of the to-be-processed medicated thread in the single-strand rope state and being driven by the third driving mechanism 320 to pull the to-be-processed medicated thread along a direction opposite to the first slideway 510, such that the to-be-processed medicated thread is folded. Further, the second driving part 313 drives the thread winding body 3121 and the winding hook assembly 3122 to rotate, such that the to-be-processed medicated thread winds and extends from middle to two ends to be twisted in the double-strand rope state.

It is worth mentioning that the contour construction of the thread winding body 3121 of the thread winding seat 312 is as same as that of the first clamping body 1121 of the first clamping seat 112. The working principle is same too, which can specifically refer to specific description. An end portion of the winding hook assembly 3122 of the thread winding seat 312 is assembled with a winding hook 31221 for hooking the center position of the to-be-processed medicated thread in the single-strand rope state. The rest constructions except the winding hook 31221 of the winding hook assembly 3122 are consistent with that of the first clamping head 1122 of the first clamping seat 112, which can specifically refer to specific description of the first clamping seat 112.

It is worth mentioning that the control apparatus 400 of the patent can include the control box 410, and the control box 410 is assembled with the display screen 411, the rotary knob 412, the zeroing button 413, the starting button 414 and the like. The first driving body 131, the second driving body 221, the third driving body 321, the first driving part 113 and the second driving part 313 are electrically connected with the control box 410 via guide wires 620. The display screen 411 is used for displaying and setting each parameter, for example, the parameter can include the farthest distance between the first clamping mechanism 110 and the second clamping mechanism 120, that is, the length of the medicated thread, such that medicated threads with different lengths can be manufactured. The parameter can further include a sliding distance of the thread winding apparatus, a sliding distance of the medicine spraying apparatus, a medicine spraying amount, a rotating number of turns of the single-strand rope, a rotating number of turns of the double-strand rope and the like, which is no longer enumerated herein. The rotary knob 412 can be used for adjusting the medicine spraying amount, the zeroing button 413 can be used for enabling the control box 410 to be in an initial state of starting to operate after each parameter is set, and the starting button 414 is used for starting the control box 410, such that the medicated thread is manufactured.

The present invention further provides a medicated thread manufacturing method, specifically including:

respectively clamping two ends of the to-be-processed medicated thread to the thread clamping apparatus 100, and controlling, by the control apparatus 400, the thread clamping apparatus 100 to straighten the to-be-processed medicated thread; determining, by the user, the length of the to-be-processed medicated thread according to an actual using demand, and then setting the farthest distance between the first clamping mechanism 110 and the second clamping mechanism 120 by operating the display screen 411, that is, the distance of the straightened medicated thread;

controlling, by the control apparatus 400, the medicine spraying apparatus 200 to spray the medicine to the surface layer of the to-be-processed medicated thread in the straightened state; determining, by the user, the medicine spraying amount according to the actual using demand, adjusting the medicine spraying amount by rotating the rotary knob 412 and increasing the medicine amount by slowing down the moving speed of the medicine spraying apparatus 200, and on the contrary, reducing the medicine amount;

controlling, by the control apparatus 400, the thread clamping apparatus 100 again in the straightened state and twisting the to-be-processed medicated thread sprayed with the medicine into the single-strand rope state, wherein the rotating number of turns can be selected according to the length of the medicated thread, the longer the medicated thread is, the greater the rotating number of turns is and on the contrary, the smaller the rotating number of turns is;

controlling, by the control apparatus 400, the thread winding apparatus 300 to abut a center position of the to-be-processed medicated thread in the single-strand rope state and pull the to-be-processed medicated thread toward a direction opposite to the first slideway 510 to fold the to-be-processed medicated thread, such that the to-be-processed medicated thread is driven to rotate, and therefore, the to-be-processed medicated thread winds and extends from middle to two ends to be twisted in the double-strand rope state. Similarly, the longer the folded medicated thread is, the greater the rotating number of turns is, and on the contrary, the smaller the rotating number of turns is.

The above examples are the preferred embodiments of the present invention. It should be noted that improvements and embellishments shall be made within the protection range of the disclosure to those skilled in the technical field without departing the principle of the present invention.

The invention claimed is:

1. A medicated thread manufacturing system, comprising:
a first slideway and a second slideway that are arranged in a T shape;
a thread clamping apparatus and a medicine spraying apparatus slidably arranged on the first slideway,
wherein the thread clamping apparatus is used for clamping two ends of a to-be-processed medicated thread, straightening the to-be-processed medicated thread and twisting the to-be-processed medicated thread in the straightened state into a single-strand rope state, and
the medicine spraying apparatus is used for spraying a medicine towards a surface layer of the to-be-processed medicated thread in the straightened state;

a thread winding apparatus slidably arranged on the second slideway, wherein the thread winding apparatus is used for abutting a center position of the to-be processed medicated thread in the single-strand rope state and pulling the to-be-processed medicated thread towards a direction opposite to the first slideway to fold the to-be-processed medicated thread, and used for rotating the to-be-processed medicated thread, such that the to-be-processed medicated thread winds and extends from middle to two ends to be twisted in a double-strand rope state; and a control apparatus in signal connection and/or electrical connection to the thread clamping apparatus, the medicine spraying apparatus and the thread winding apparatus.

2. A medicated thread manufacturing method for a medicated thread manufacturing system according to claim 1, the method comprising:

clamping two ends of a to-be-processed medicated thread to the thread clamping apparatus;

controlling, by the control apparatus, the thread clamping apparatus to straighten the to-be-processed medicated thread;

controlling, by the control apparatus, the medicine spraying apparatus to spray a medicine toward a surface layer of the to-be-processed medicated thread in the straightened state;

controlling, by the control apparatus, the thread clamping apparatus again to twist the to-be-processed medicated thread sprayed with the medicine into the single-strand rope state; and controlling, by the control apparatus, the thread winding apparatus to abut a center position of the to-be-processed medicated thread in the single-strand rope state and pull the to-be-processed medicated thread toward a direction opposite to the first slideway to fold the to-be-processed medicated thread, such that the to-be-processed medicated thread is driven to rotate, and therefore, the to-be-processed medicated thread winds and extends from middle to two ends to be twisted in the double-strand rope state.

3. The medicated thread manufacturing system according to claim 1, wherein the first slideway is provided with a first slide rail and a second slide rail that are arranged parallelly;

the thread clamping apparatus is slidably arranged on the first slide rail; and the medicine spraying apparatus is slidably arranged on the second slide rail.

4. The medicated thread manufacturing system according to claim 3, wherein the medicine spraying apparatus comprises a medicine spraying mechanism and a second driving mechanism that drives the medicine spraying mechanism to operate;

the medicine spraying mechanism comprises a third sliding seat, a supporting rack, a spraying part, a spraying driving part and a liquid storage device;

the third sliding seat is slidably connected to the second slide rail, the supporting rack is assembled on the third sliding seat, the spraying part is assembled on the supporting rack and is used for spraying a medicine to a surface layer of the to-be-processed medicated thread, the spraying driving part is assembled on the supporting rack, is in signal connection and/or electrical connection to the control apparatus and is used for controlling and driving the spraying part to operate, and the liquid storage device is assembled on the supporting rack and/or the third sliding seat, is located directly below a spraying port of the spraying part and is used for collecting a residual liquid; and the second driving mechanism comprises a second driving body, two second belt wheels and a second conveyor belt;

the second driving body is assembled at one end of the first slideway and is in signal connection and/or electrical connection to the control apparatus, one of the second belt wheels is assembled at the driving end of the second driving body and corresponds to a position of the second slide rail, the other one of second belt wheels is assembled at the other end of the second slideway via a second fixing part and the two second belt wheels are arranged oppositely, and the second conveyor belt is arranged on the two second belt wheels in a sleeving manner and is located above a center line of the second slide rail; and wherein the third sliding seat is fixed to the second conveyor belt, such that during a process where the second driving body drives the second conveyor belt to rotate, and the second conveyor belt drives the medicine spraying mechanism to move back and forth along the second slide rail so as to further spray the medicine to the surface layer of the to-be-processed medicated thread in the straightened state.

5. The medicated thread manufacturing system according to claim 3, wherein the thread clamping apparatus comprises a first clamping mechanism, a second clamping mechanism and a first driving mechanism;

both the first clamping mechanism and the second clamping mechanism are in signal connection and/or electrical connection to the control apparatus, both the first clamping mechanism and the second clamping mechanism are slidably connected to the first slide rail and are used for clamping two ends of the to-be-processed medicated thread respectively, and the first driving mechanism is assembled at one end of the first slide rail and is used for driving the first clamping mechanism and the second clamping mechanism to move close to each other or far away from each other; and wherein when the to-be-processed medicated thread is in the straightened state, the first clamping mechanism is further used for twisting the to-be-processed medicated thread into the single-strand rope state.

6. The medicated thread manufacturing system according to claim 5, wherein the first clamping mechanism comprises a first sliding seat, a first clamping seat and a first driving part;

the second clamping mechanism comprises a second sliding seat and a second clamping seat;

both the first sliding seat and the second sliding seat are slidably connected to the first slide rail, the first driving part is in signal connection and/or electrical connection to the control apparatus and is assembled on the first slide rail and the first clamping seat is assembled at a driving end of the first driving part, and the second clamping seat is assembled on the second sliding seat and is arranged opposite to the first clamping seat; and wherein the first clamping seat and the second clamping seat are used for clamping two ends of the to-be-processed medicated thread respectively, and when the to-be-processed medicated thread is in the straightened state, the first driving part drives the first clamping seat to rotate to twist the to-be-processed medicated thread into the single-strand rope state.

7. The medicated thread manufacturing system according to claim 6, wherein the first clamping mechanism comprises a first clamping body and a first clamping head;

the first clamping body is assembled at the driving end of the first driving part, the first clamping head is elastically assembled at an end, opposite to the first driving part, of the first clamping body, the first clamping head is used for clamping one end of the to-be-processed medicated thread, and moves toward the second clamping seat under the action of a tensile force of the to-be-processed medicated thread and is restored to an initial position under the action of an elastic force after the tensile force is canceled; and the second clamping mechanism comprises a second clamping body and second clamping head;

the second clamping body is assembled on the second sliding seat, the second clamping head is elastically assembled at an end, facing the second clamping body, of the second clamping body, the second clamping head is used for clamping the other end of the to-be-processed medicated thread, and moves toward the first clamping seat under the action of a tensile force of the to-be-processed medicated thread and is restored to the initial position under the action of the elastic force after the tensile force is canceled; and wherein during a process wherein the to-be-processed medicated thread in the straightened state is twisted into the single-strand rope state, a length thereof is shortened gradually, and the first clamping head and the second clamping head provide an elastic force for keeping the to-be-processed medicated thread tight.

8. The medicated thread manufacturing system according to claim 6, wherein the first driving mechanism comprises a first driving body, two first belt wheels and a first conveyor belt;

the first driving body is assembled at one end of the first slideway and is in signal connection and/or electrical connection to the control apparatus, one of the first belt wheels is assembled at the driving end of the first driving body and corresponds to a position of the first slide rail, the other one of the first belt wheels is assembled at the other end of the first slideway via a first fixing part and the two first belt wheels are arranged oppositely, and the first conveyor belt is arranged on the two first belt wheels in a sleeving manner and is located above a center line of the first slide rail; and wherein one of the first slideway and the second slideway is fixed to an upper portion of the first conveyor belt and the other one is fixed to a lower portion of the first conveyor belt, such that during a process where the first driving body drives the first conveyor belt to rotate, the first conveyor belt drives the first sliding seat and the second sliding seat to move close to each other or far away from each other.

9. The medicated thread manufacturing system according to claim 5, wherein the thread winding apparatus comprises a thread winding mechanism and a third driving mechanism that drives the thread winding mechanism to operate;

the thread winding mechanism comprises a fourth sliding seat, a thread winding seat and a second driving part, the fourth sliding seat is slidably connected to the second slideway, the second driving part is in signal connection and/or electrical connection to the control apparatus and is assembled on the fourth sliding seat, and the thread winding seat is assembled at a driving end of the second driving part;

the third driving mechanism comprises a third driving body, two third belt wheels and a third conveyor belt, the third driving body is assembled at the end, opposite to the first slideway, of the second slideway and is in signal connection and/or electrical connection to the control apparatus, one of third belt wheels is assembled at the driving end of the third driving body and the other one of second belt wheels is assembled at the other end of the second slideway via a third fixing part and the two second belt wheels are arranged oppositely, and the third conveyor belt is arranged on the two third belt wheels in a sleeving manner and is located above a center line of the second slide rail; and wherein the fourth sliding seat is fixed to the third conveyor belt, during a process where the third driving body drives the third conveyor belt to rotate, the third conveyor belt drives the fourth sliding seat to move back and forth along the second slideway, such that the thread winding seat abuts a center position of the to-be-processed medicated thread in the single-strand rope state and the to-be-processed medicated thread is pulled toward a direction opposite to the first slideway to fold, the to-be-processed medicated thread, and the second driving part drives the thread winding seat to rotate so as to further drive the to-be-processed medicated thread to rotate, such that the to-be-processed medicated thread winds and extends from middle to two ends to be twisted in a double-strand rope state.

10. The medicated thread manufacturing system according to claim 9, wherein the thread winding seat comprises a thread winding body and a winding hook assembly;

the thread winding body is assembled at the driving end of the second driving part, the winding hook assembly is elastically assembled at an end, opposite to the second driving part, of the thread winding body, the winding hook assembly moves toward the first slideway under the action of a tensile force and is restored to an initial position under the action of an elastic force after the tensile force is canceled; and wherein the winding hook assembly is used for abutting the center position of the to-be-processed medicated thread in the single-strand rope state and used for pulling the to-be-processed medicated thread along a direction opposite to the first slideway when being driven by the third driving mechanism, such that the to-be-processed medicated thread is folded; and the second driving part drives the thread winding body and the winding hook assembly to rotate, such that the to-be-processed medicated thread winds and extends from middle to two ends to be twisted in the double-strand rope state.

* * * * *